(12) United States Patent
Tang et al.

(10) Patent No.: US 11,815,457 B2
(45) Date of Patent: Nov. 14, 2023

(54) NEAR-INFRARED CHEMILUMINESCENCE EMITTER WITH AGGREGATION-INDUCED EMISSION PROPERTIES

(71) Applicant: The Hong Kong University of Science and Technology, Hong Kong (CN)

(72) Inventors: Benzhong Tang, Hong Kong (CN); Liang Luo, Hong Kong (CN); Chenchen Liu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 493 days.

(21) Appl. No.: 17/249,369

(22) Filed: Mar. 1, 2021

(65) Prior Publication Data
US 2021/0293713 A1   Sep. 23, 2021

Related U.S. Application Data

(60) Provisional application No. 63/100,562, filed on Mar. 18, 2020.

(51) Int. Cl.
| | |
|---|---|
| *G01N 21/64* | (2006.01) |
| *G01N 21/359* | (2014.01) |
| *C07D 417/04* | (2006.01) |
| *A61K 49/00* | (2006.01) |
| *B82Y 30/00* | (2011.01) |
| *B82Y 5/00* | (2011.01) |
| *B82Y 40/00* | (2011.01) |
| *B82Y 15/00* | (2011.01) |

(52) U.S. Cl.
CPC ...... *G01N 21/6456* (2013.01); *A61K 49/0093* (2013.01); *C07D 417/04* (2013.01); *G01N 21/359* (2013.01); *B82Y 5/00* (2013.01); *B82Y 15/00* (2013.01); *B82Y 30/00* (2013.01); *B82Y 40/00* (2013.01); *G01N 2223/406* (2013.01); *G01N 2223/6126* (2013.01)

(58) Field of Classification Search
CPC .................................................. G01N 21/6456
USPC ......................................................... 544/233
See application file for complete search history.

(56) References Cited

FOREIGN PATENT DOCUMENTS

CN   108727277 A   11/2018

OTHER PUBLICATIONS

J. Han, J. Jose, E. Mei, K. Burgess, Chemiluminescent Energy-Transfer Cassettes Based on Fluorescein and Nile Red. Angew Chem Int Ed Engl 2007, 46, 1684-1687.
S. Zhang, H. Cui, M. Gu, N. Zhao, M. Cheng, J. Lv, Real-Time Mapping of Ultratrace Singlet Oxygen in Rat during Acute and Chronic Inflammations via a Chemiluminescent Nanosensor. Small 2019, 15, e1804662.
Chenchen Liu et al., Near-Infrared AIE Dots with Chemiluminescence for Deep-Tissue Imaging, Adv.Mater, vol. 32, No. 43, pp. 1-6.
First Office Action of CN2021102265736 issued from the China National Intellectual Property Administration dated Apr. 27, 2023.

*Primary Examiner* — Taofiq A Solola
(74) *Attorney, Agent, or Firm* — S&F/WEHRW

(57) ABSTRACT

Compounds including triphenylamine and luminol moieties exhibiting near-infrared chemiluminescence useful as reactive oxygen sensors, pharmaceutical compositions including the same, and methods of preparation and use thereof.

20 Claims, 5 Drawing Sheets

NEAR-INFRARED CHEMILUMINESCENCE EMITTER WITH AGGREGATION-INDUCED EMISSION PROPERTIES

CROSS-REFERENCE TO RELATED APPLICATIONS

This application claims the benefit of priority of U.S. Provisional Application No. 63/100,562, filed on Mar. 18, 2020, the contents of which being hereby incorporated by reference in their entirety for all purposes.

TECHNICAL FIELD

The present disclosure generally relates to chemical structures exhibiting aggregation-induced emission properties and methods of preparation and use thereof.

BACKGROUND

Fluorescence (FL) is quite promising in real-time visualizing biomedical process with great sensitivity and high resolution. However, the penetration depth of FL is rather limited due to the requirement of excitation light and the autofluorescence from the biological structures. Although red and near-infrared (NIR) FL materials are popularly developed to reduce the tissue autofluorescence, to achieve high penetration depth still remains a great challenge, especially considering the inadequate penetration of excitation light. In contrast, chemiluminescence (CL) usually has a higher penetration depth than FL, because no excitation light is required and the background autofluorescence can be avoided, therefore holding great promise for deep-tissue imaging.

The energy required to generate visible or NIR CL emission (400-1000 nm) is around 30-70 kcal mol$^{-1}$, while the opening reaction of peroxide group can release energy of around 60 kcal mol$^{-1}$, so that peroxide groups (—O—O—) are frequently utilized in CL reactions. For example, when the well-known CL emitter luminol is oxidized by reactive oxygen species (ROS), blue light can be observed during the decomposition of unstable peroxide intermediate. However, blue light is typically limited in tissue penetration. It is crucial to transfer the blue emission of luminol into the NIR region for enhanced penetration depth and efficiency, through deliberate molecular design principles.

The CL emission originates from the excited reaction product or the excited fluorescent acceptor through energy transfer. If CL comes from the fluorescent product, the CL quantum yield ($\Phi_{CL}$) is expressed as:

$$\Phi_{CL} = \Phi_R \times \Phi_{ES} \times \Phi_F \quad (1)$$

where $\Phi_R$ is the reaction yield, $\Phi_{ES}$ reflects the ratio of the product accessing the excited state and $\Phi_F$ is the fluorescent quantum yield of the reaction product. The CL-generating reaction of luminol involves many electron-rich intermediates like anions and radicals, so the reaction yield can be enhanced by conjugating electron-withdrawing groups. Benzothiadiazole used herein is a strong electron acceptor that has been widely utilized in organic solar cells and organic light emitting diodes, and it can efficiently facilitate CL generation after being conjugated with luminol. In addition, many hydrophobic organic dyes suffer from aggregation-caused quenching (ACQ) effect due to strong π-π stacking, and the emission could be largely quenched in aqueous solutions. For example, the solubility and fluorescent quantum yield of the Nile red-based luminol cassette are relatively low in water, which restricts its further application in biological systems. In contrast, fluorophores with aggregation-induced emission (AIE) properties exhibit intense emission in the aggregation state due to the restriction of molecular motion, making them more favorable for bioimaging. Moreover, the addition of the electron-donating group triphenylamine can form a donor-acceptor structure, and enable the bathochromic shift of the emission of luminol-containing fluorophore.

In addition, if the CL emission is generated from the acceptor fluorophore by energy transfer, the fluorescent quantum yield of the acceptor ($\Phi'_F$) and the energy transfer efficiency ($\Phi_{ET}$) should be taken into consideration as well.

$$\Phi_{CL} = \Phi_{ES} \times \Phi'_F \times \Phi_{ET} \quad (2)$$

The through-bond energy transfer was reported to be more efficient than the through-space energy transfer. Although some NIR CL systems have been developed by physically encapsulating the CL emitters with the NIR fluorescent materials in surfactant micelles, the preparation process is rather complicated and phase separation may occur during the long-term storage. More importantly, the energy transfer efficiency is much lower than the chemical conjugation system.

SUMMARY

The present disclosure relates to a novel class of near-infrared (NIR) chemiluminescence (CL) emitters having Formula 1, exemplified by triphenylamine-combined benzothiadiazole (TBL), which were designed and synthesized by chemically conjugating luminol with benzothiadiazole and triphenylamine. The electron-withdrawing group benzothiadiazole can facilitate the CL process, and the aggregation-induced emission (AIE) property of TBL ensures high NIR CL emission of TBL dots in aqueous solutions. In vitro and in vivo experiments have been conducted to evaluate the potential application of TBL dots for $^1O_2$ detection in real biological systems. The NIR CL emission could penetrate through 3 cm-thick pork ham, showing great advantages over FL and blue CL emission. Furthermore, the successful differentiation of tumor and normal tissues demonstrated the potential of this system for CL-guided cancer diagnosis and surgery.

In a first aspect, provided herein is a compound having Formula 1:

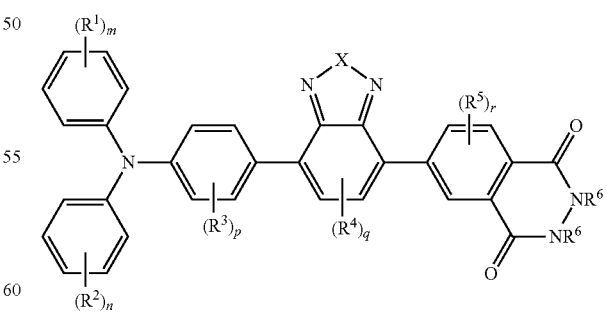

or a pharmaceutically acceptable salt thereof, wherein
each of m and n are independently a whole number selected from 1-5;
p if a whole number selected from 1-4;
q is a whole number selected from 1-2;

r is a whole number selected from 1-3;

t is a whole number selected from 0-6;

X is O, S, or $NR^7$;

each of $R^1$, $R^2$, $R^3$, $R^4$, and $R^5$ for each occurrence is independently selected from the group consisting of hydrogen, halide, nitrile, nitro, —OR, —SR, —$NR_2$, —(C=O)R, —(C=O)OR, —(C=O)$NR_2$, —N(R)(C=O)R, —O(C=O)R, —N(R)(C=O)OR, —N(R)(C=O)$NR_2$, —O(C=O)$NR_2$, —(S=O)R, —$SO_2R$, —$SO_2OR$, —$SO_2NR_2$, —N(R)$SO_2R$, alkyl, cycloalkyl, alkenyl, alkynyl, aryl, heterocycloalkyl, heteroaryl, and —$(CH_2)_tR^8$;

$R^6$ for each occurrence is independently hydrogen, alkyl, cycloalkyl, alkenyl, alkynyl, aryl, heterocycloalkyl, or heteroaryl;

$R^7$ for each occurrence is independently hydrogen, alkyl, cycloalkyl, alkenyl, alkynyl, aryl, heterocycloalkyl, or heteroaryl;

$R^8$ for each occurrence is independently —$N_3$, —OH, —$CO_2H$, —$NH_2$, —C≡CH, —Br, —I, or N-maleimide; and R for each occurrence is independently hydrogen, alkyl, cycloalkyl, alkenyl, alkynyl, aryl, heterocycloalkyl, or heteroaryl.

In certain embodiments, each of m, n, p, and r is 1.

In certain embodiments, each of $R^1$, $R^2$, $R^3$, $R^4$, and $R^5$ is independently for each occurrence is independently selected from the group consisting of hydrogen, halide, —OR, —$NR_2$, —N(R)(C=O)R, —O(C=O)R, —N(R)(C=O)OR, —N(R)(C=O)$NR_2$, alkyl, cycloalkyl, aryl, heterocycloalkyl, and heteroaryl.

In certain embodiments, each of $R^1$ and $R^2$ is independently for each occurrence is independently selected from the group consisting of hydrogen, —OR, —$NR_2$, —N(R)(C=O)R, —O(C=O)R, —N(R)(C=O)OR, —N(R)(C=O)$NR_2$, alkyl, aryl, heterocycloalkyl, and heteroaryl; and $R^4$ is halide.

In certain embodiments, X is O, S, or $NR^7$, wherein $R^7$ is hydrogen or alkyl.

In certain embodiments, the compound has Formula 2:

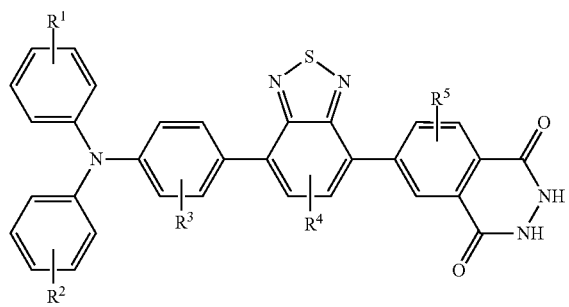

2 wherein each of $R^1$, $R^2$, $R^3$, $R^4$, and $R^5$ is independently hydrogen, F, alkyl, unsaturated alkyl, heteroalkyl, cycloalkyl, heterocycloalkyl, aryl, heteroaryl, carboxyl group, amino group, sulfonic group, alkylthio, or alkoxy group.

In certain embodiments, the compound has Formula 3:

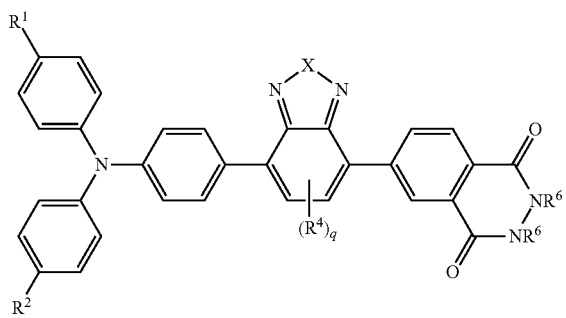

3 or a pharmaceutically acceptable salt thereof, wherein q is a whole number selected from 1-2;

t is a whole number selected from 0-6;

X is O, S, or $NR^7$;

each of $R^1$ and $R^2$ for each occurrence is independently selected from the group consisting of hydrogen, halide, nitrile, nitro, —OR, —SR, —$NR_2$, —(C=O)R, —(C=O)OR, —(C=O)$NR_2$, —N(R)(C=O)R, —O(C=O)R, —N(R)(C=O)OR, —N(R)(C=O)$NR_2$, —O(C=O)$NR_2$, —(S=O)R, —$SO_2R$, —$SO_2OR$, —$SO_2NR_2$, —N(R)$SO_2R$, alkyl, cycloalkyl, alkenyl, alkynyl, aryl, heterocycloalkyl, heteroaryl, and —$(CH_2)_tR^8$;

$R^4$ is hydrogen, alkyl, or halide;

$R^6$ for each occurrence is independently hydrogen or alkyl;

$R^7$ for each occurrence is independently hydrogen or alkyl;

$R^8$ for each occurrence is independently —$N_3$, —OH, —$CO_2H$, —$NH_2$, —C≡CH, —Br, —I, or N-maleimide; and R for each occurrence is independently hydrogen, alkyl, cycloalkyl, alkenyl, alkynyl, aryl, heterocycloalkyl, or heteroaryl.

In certain embodiments, X is S; each of $R^1$ and $R^2$ is —OR; and $R^4$ and $R^6$ is hydrogen.

In certain embodiments, the compound is:

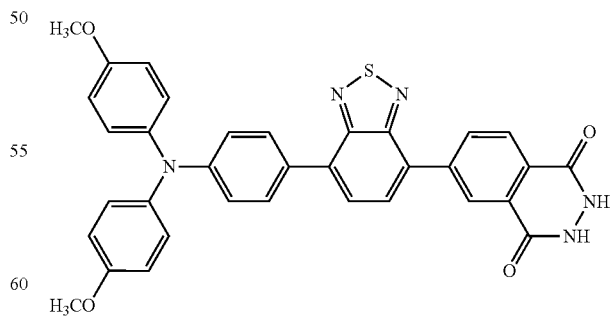

or a pharmaceutically acceptable salt thereof.

In a second aspect, provided herein is a the method of preparing a compound described herein, the method comprising: contacting a compound of Formula 4:

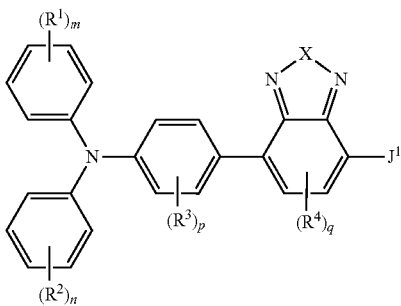

or a pharmaceutically acceptable salt thereof, wherein
each of m and n are independently a whole number selected from 0-5;
p if a whole number selected from 1-4;
q is a whole number selected from 1-2;
t is a whole number selected from 0-6;
$J^1$ is halide, mesylate, tosylate, triflate, —B(OR$^9$)$_2$ or —Sn(R$^{10}$)$_3$;
X is O, S, or NR$^7$;
each of R$^1$, R$^2$, R$^3$, and R$^4$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, and —(CH$_2$)$_t$R$^8$;
R$^7$ for each occurrence is independently hydrogen, alkyl, cycloalkyl, alkenyl, alkynyl, aryl, heterocycloalkyl, or heteroaryl;
R$^8$ for each occurrence is independently —N$_3$, —OH, —CO$_2$H, —NH$_2$, —C≡CH, —Br, —I, or N-maleimide; and
R for each occurrence is independently hydrogen, alkyl, cycloalkyl, alkenyl, alkynyl, aryl, heterocycloalkyl, or heteroaryl;
a compound of Formula 5:

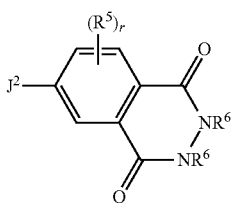

r is a whole number selected from 1-3;
$J^2$ is halide, mesylate, tosylate, triflate, —B(OR$^9$)$_2$, or —Sn(R$^{10}$)$_3$;
R$^5$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, and —(CH$_2$)$_t$R$^8$;

R$^6$ for each occurrence is independently hydrogen, alkyl, cycloalkyl, alkenyl, alkynyl, aryl, heterocycloalkyl, or heteroaryl;
R$^9$ is hydrogen, alkyl, cycloalkyl, or aryl; or two instances of R$^9$ together with the oxygen to which they are attached form a 5-6 membered optionally heterocylic ring; and
R$^{10}$ for each occurrence is independently alkyl; and
a catalyst thereby forming a compound described herein, wherein if $J^1$ is halide, mesylate, tosylate, or triflate, then $J^2$ is —B(OR$^9$)$_2$ or —Sn(R$^{10}$)$_3$; and if $J^1$ is —B(OR$^9$)$_2$ or —Sn(R$^{10}$)$_3$, then $J^2$ is halide, mesylate, tosylate, or triflate.

In a third aspect, provided herein is a nanoparticle comprising a compound described herein.

In certain embodiments, the nanoparticle further comprises a non-ionic surfactant.

In certain embodiments, the non-ionic surfactant is a polyalkylene glycol.

In certain embodiments, the average hydrodynamic size of the nanoparticle in phosphate buffered saline solution at pH 7.4 is between 10-100 nm.

In a fourth aspect, provided herein is a pharmaceutical composition comprising a compound described herein and at least one pharmaceutically acceptable excipient.

In a fifth aspect, provided herein is a method of detecting a reactive oxygen species in a sample suspected of containing the reactive oxygen species, the method comprising: contacting the sample with a compound described herein and detecting the chemiluminescence of the compound.

In certain embodiments, the method further comprises determining the concentration of the reactive oxygen species in the sample based on the detected intensity of chemiluminescence.

In a sixth aspect, provided herein is a method of imaging tissue comprising a reactive oxygen species in a subject, the method comprising: administering a compound described herein to the subject and detecting the chemiluminescence of the compound.

In certain embodiments, the compound is administered by injection to the tissue.

In certain embodiments, the tissue comprises a cancer cell.

BRIEF DESCRIPTION OF DRAWINGS

The above and other objects and features of the present disclosure will become apparent from the following description of the disclosure, when taken in conjunction with the accompanying drawings.

DETAILED DESCRIPTION

Definitions

Figure 1:
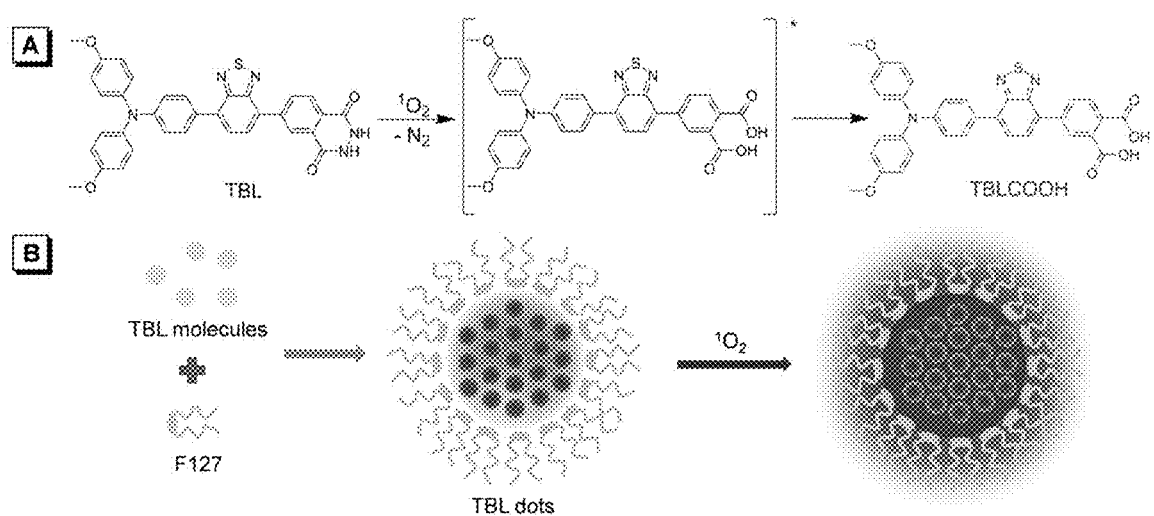
FIG. 1 depicts (A) the proposed CL generation mechanism of TBL oxidized by $^1O_2$; and (B) a schematic illustration of the preparation of TBL dots and the generation of CL.
Figure 2:
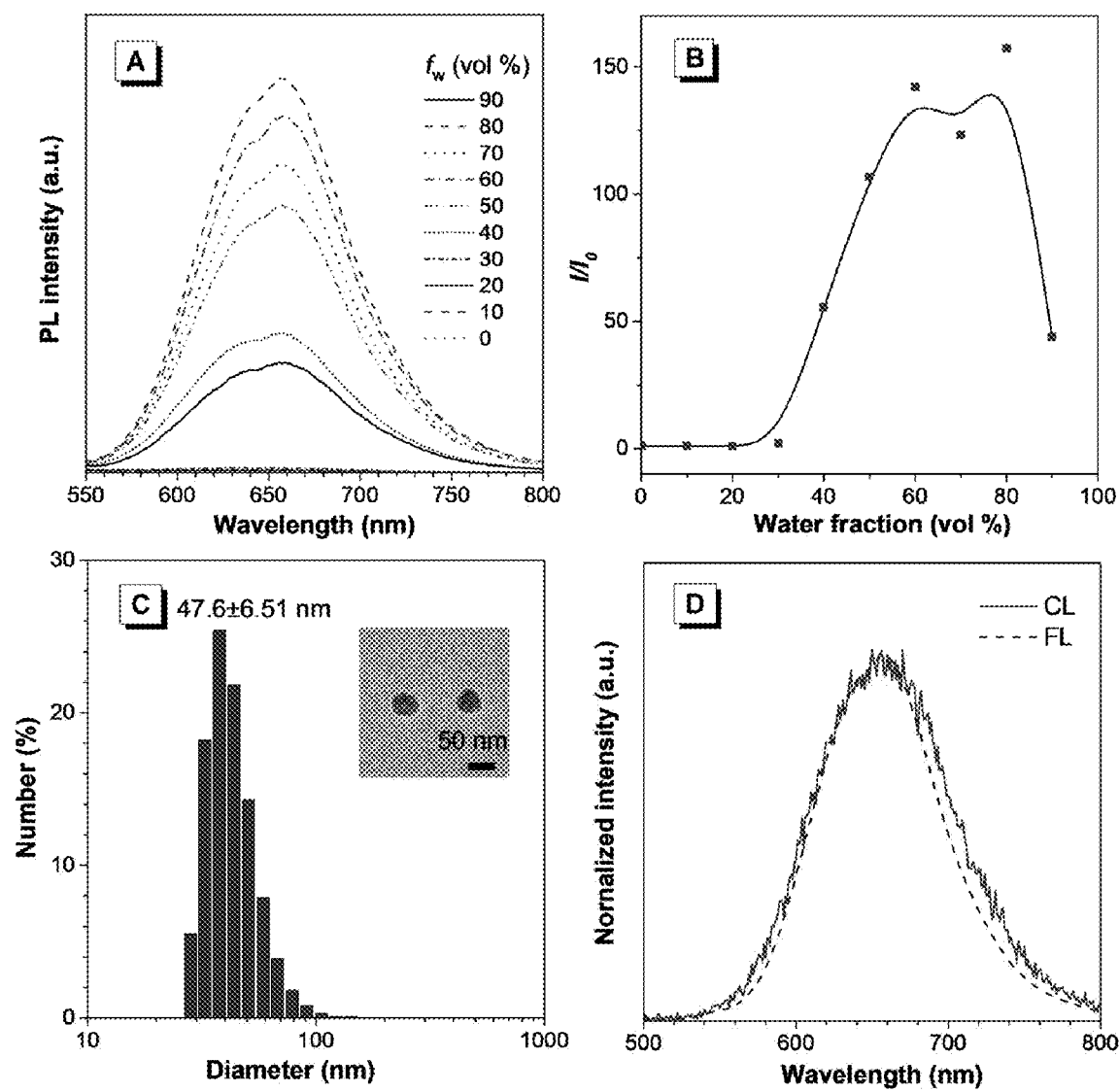
FIG. 2 depicts (A) the PL spectra of TBL ($10^{-5}$ M) in different DMSO/H$_2$O mixtures with the addition of water ($\lambda_{ex}$: 460 nm); (B) the plot of relative maximum emission intensity (I/I$_0$) of TBL in different DMSO/H$_2$O mixtures; (C) the hydrodynamic size distribution of TBL dots in PBS solution (pH=7.4)—Inset: TEM image of TBL dots; and (D) the normalized FL and CL spectra of TBL dots.
Figure 3:
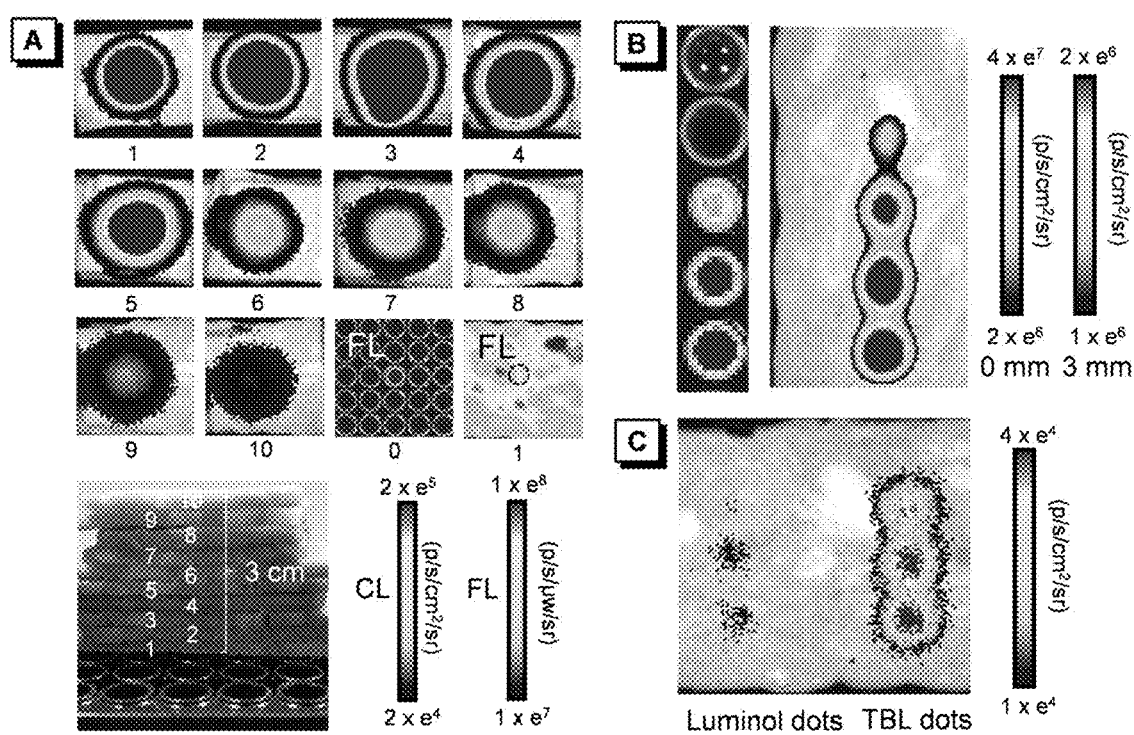
FIG. 3 depicts (A) CL images of TBL dots (2 mM) with $^1O_2$ (150 mM) and FL images of TBL dots (2 mM) covered by different slices of pork ham. The thickness of one slice pork ham is around 3 mm. Binning: 8; Exposure time: 4 min; f/Stop:1; (B) CL images of TBL dots (2 mM) with different concentration of $^1O_2$ (left) and covered with one slice of ~3.0 mm-thick pork ham (right), the concentration of $^1O_2$ is $5\times10^{-4}$ M, $1\times10^{-3}$ M, $2.5\times10^{-3}$ M, $5\times10^{-3}$ M, $1\times10^{-2}$ M from top to bottom. Binning: 4; Exposure time: 0.5 min; f/Stop:1; and (C) CL images of Luminol dots (1.2 mM) and TBL dots (1.2 mM) with $^1O_2$ (8 mM) covered by one slice of ~3.0 mm-thick pork ham. Binning: 4; Exposure time: 4 min; f/Stop: 1.
Figure 4:
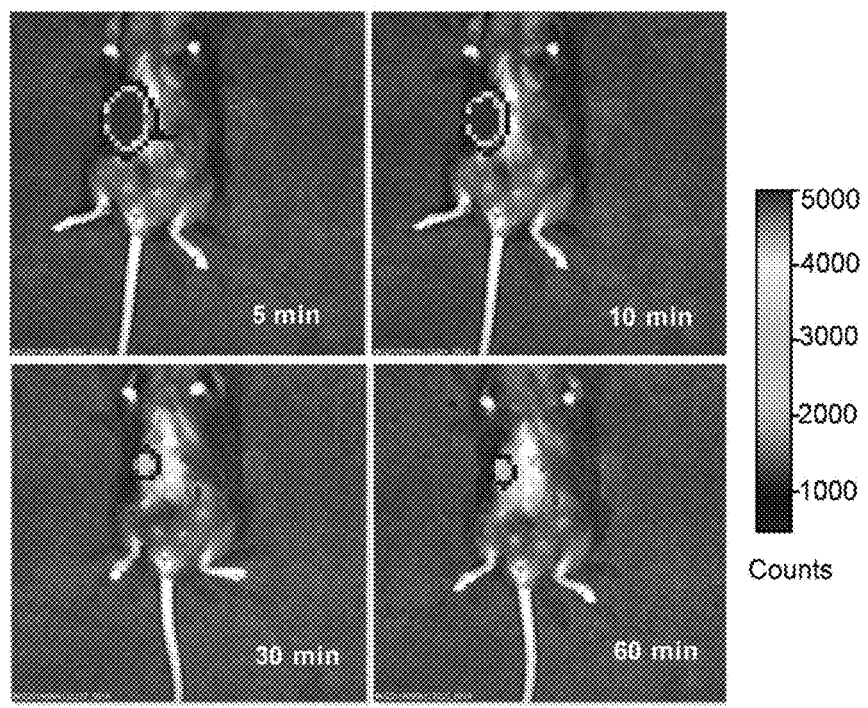
FIG. 4 depicts in vivo images of CL signals in hair-shaved mice (left-side body) after subcutaneous injection of TBL dots (2 mM, 50 µL) with $H_2O_2$ (1 mM, 50 µL) and NaClO (1 mM, 50 µL) for 5 min, 10 min, 30 min and 60 min. Binning: 16; Exposure time: 1 min; f/Stop:1.
Figure 5:
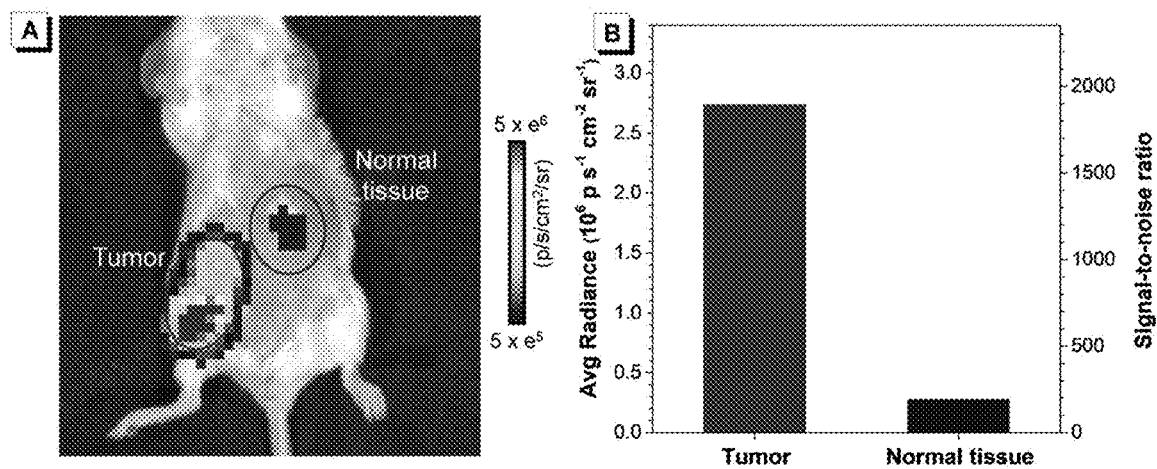
FIG. 5 depicts (A) in vivo CL images; and (B) the intensity and signal-to-noise ratio of tumor (left) and normal tissue (right) after injection of TBL dots (2 mM, 200 µL) with $H_2O_2$ (400 mM, 50 µL). Binning: 16; Exposure time: 2 s; f/Stop:1.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

It should be understood that the order of steps or order for performing certain actions is immaterial so long as the present teachings remain operable. Moreover, two or more steps or actions may be conducted simultaneously.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

As used herein, unless otherwise indicated, the term "halo" or "halide" includes fluoro, chloro, bromo or iodo.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., C1-40 alkyl group), for example, 1-30 carbon atoms (i.e., C1-30 alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In certain embodiments, alkenyl groups can be substituted as described herein. An alkenyl group is generally not substituted with another alkenyl group, an alkyl group, or an alkynyl group.

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

The terms "heterocycloalkyl" or "heterocyclyl" as used herein, alone or in combination, refers to a non-aromatic, mono- or poly-cyclic ring system in which one or more of the atoms in the ring system is an element other than carbon, such as nitrogen, oxygen or sulfur, alone or in combination, and wherein the ring system is optionally substituted. Any suitable ring position of the heterocycloalkyl group can be covalently linked to the defined chemical structure. In certain embodiments, a heteroatom can occupy the position at which the heterocycle is attached to the defined chemical structure. Thus, one of ordinary skill in the art will understand that the connection of said heterocycloalkyl ring can be through a carbon or a $sp^3$ hybridized nitrogen heteroatom. Examples of heterocycloalkyls include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, pyrrolidinyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, piperazinyl, chromanyl, and the like.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In certain embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In certain embodiments, aryl groups can be optionally substituted. In certain embodiments, an aryl group can have one or more halogen substituents, and can be referred to as a "haloaryl" group. Perhaloaryl groups, i.e., aryl groups where all of the hydrogen atoms are replaced with halogen atoms (e.g., $—C_6F_5$), are included within the definition of "haloaryl." In certain embodiments, an aryl group is substituted with another aryl group and can be referred to as a biaryl group. Each of the aryl groups in the biaryl group can be optionally substituted.

The term "aralkyl" refers to an alkyl group substituted with an aryl group.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In certain embodiments, heteroaryl groups can be substituted as described herein. In certain embodiments, heteroaryl groups can be optionally substituted.

The term "optionally substituted" refers to a chemical group, such as alkyl, cycloalkyl aryl, and the like, wherein one or more hydrogen may be replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $—CF_3$, $—CN$, or the like The term "carbocycle" is art-recognized and refers to an aromatic or non-aromatic ring in which each atom of the ring is carbon.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counter ions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

The phrase "aggregation-induced emission" or "AIE" as used herein refers to the enhancement of light-emission by a fluorescent compound upon aggregation in the amorphous or crystalline (solid) states of the fluorescent compound, whereas the fluorescent compound exhibits weak or substantially no emission in dilute solutions.

The term "$\lambda_{ex}$" as used herein refers to the excitation wavelength.

The term "$\lambda_{em}$" as used herein refers to the emission wavelength.

The term "sample" as used herein relates to a material or mixture of materials, typically, although not necessarily, in fluid form, but can also be in solid or gaseous form, suspected of containing the reactive oxygen species. In certain embodiments, the sample are derived from a variety of sources such as food stuffs, environmental materials (e.g., soil, air, water, and the like), or a biological such as a body fluid, a sample from a tissue or an organ, or a sample of wash/rinse fluid or a swab or smear obtained from an outer or inner body surface. In certain embodiments, samples of stool, urine, saliva, cerebrospinal fluid, blood, serum, plasma, or lacrimal fluid are encompassed as samples by the methods described herein.

The present disclosure provides a compound of Formula 1:

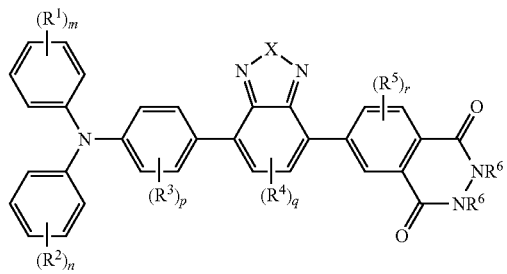

or a pharmaceutically acceptable salt thereof, wherein
each of m and n are independently a whole number selected from 1-5;
p if a whole number selected from 1-4;
q is a whole number selected from 1-2;
r is a whole number selected from 1-3;
t is a whole number selected from 0-6;
X is O, S, or $NR^7$;
each of $R^1$, $R^2$, $R^3$, $R^4$, and $R^5$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, and —(CH$_2$)$_t$R$^8$;
$R^6$ for each occurrence is independently hydrogen, alkyl, cycloalkyl, alkenyl, alkynyl, aryl, heterocycloalkyl, or heteroaryl;
$R^7$ for each occurrence is independently hydrogen, alkyl, cycloalkyl, alkenyl, alkynyl, aryl, heterocycloalkyl, or heteroaryl;
$R^8$ for each occurrence is independently —N$_3$, —OH, —CO$_2$H, —NH$_2$, —C≡CH, —Br, —I, or N-maleimide; and
R for each occurrence is independently hydrogen, alkyl, cycloalkyl, alkenyl, alkynyl, aryl, heterocycloalkyl, or heteroaryl.

In certain embodiments, each of m and n are independently a whole number selected from 1-5, 1-4, 1-3, 1-2, or 1.

In certain embodiments, p if a whole number selected from 1-4, 1-3, 1-2, or 1.

In certain embodiments, q is a whole number selected from 1-2 or 1.

In certain embodiments, r is a whole number selected from 1-3, 1-2, or 1.

In certain embodiments, t is a whole number selected from 0-6, 0-5, 0-4, 0-3, 0-2, 2-6, 2-5, or 2-4.

In certain embodiments, each of $R^1$ and $R^2$ for each occurrence is independently selected from the group consisting of hydrogen, —OR, —SR, —NR$_2$, —N(R)(C=O)R, —O(C=O)R, —N(R)(C=O)OR, —N(R)(C=O)NR$_2$, —O(C=O)NR$_2$, —SO$_2$OR, alkyl, cycloalkyl, aryl, heterocycloalkyl, heteroaryl, and —(CH$_2$)$_t$R$^8$. In certain embodiments, each of R$^1$ and R$^2$ is —OR.

In certain embodiments, R$^3$ is selected from the group consisting of hydrogen, halide, nitrile, nitro, —OR, —NR$_2$, alkyl, cycloalkyl, aryl, heterocycloalkyl, and heteroaryl. In certain embodiments, R$^3$ is hydrogen.

In certain embodiments, R$^4$ is selected from the group consisting of hydrogen, halide, nitrile, nitro, —(C=O)R, —(C=O)OR, —(C=O)NR$_2$, —(S=O)R, —SO$_2$R, —SO$_2$OR, and —SO$_2$NR$_2$. In certain embodiments, R$^4$ is hydrogen or a halide selected from fluoride and chloride.

In certain embodiments, R$^5$ is selected from the group consisting of hydrogen, halide, nitrile, nitro, —OR, —NR$_2$, alkyl, cycloalkyl, aryl, heterocycloalkyl, and heteroaryl. In certain embodiments, R$^5$ is hydrogen.

In certain embodiments, R$^6$ is hydrogen or C$_1$-C$_6$ alkyl. In certain embodiments, R$^6$ is hydrogen.

In certain embodiments, R$^7$ is C$_1$-C$_{16}$ alkyl, C$_1$-C$_{12}$ alkyl, C$_1$-C$_8$ alkyl, or C$_1$-C$_6$ alkyl.

In certain embodiments, the compound has Formula 2:

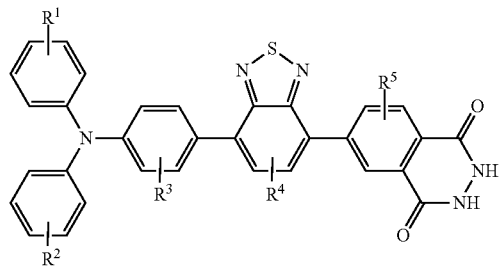

or pharmaceutically acceptable salt thereof, wherein each of R$^1$, R$^2$, R$^3$, R$^4$, and R$^5$ is independently as defined in any embodiment described herein.

In certain embodiments, the compound has Formula 2, wherein each of R$^1$, R$^2$, R$^3$, R$^4$, and R$^5$ is independently hydrogen, F, alkyl, unsaturated alkyl, heteroalkyl, cycloalkyl, heterocycloalkyl, aryl, heteroaryl, carboxyl group, amino group, sulfonic group, alkylthio, or alkoxy group.

In certain embodiments, the compound has Formula 2:

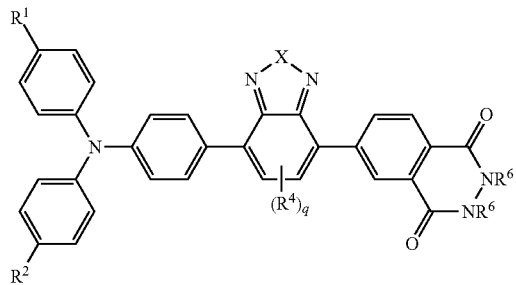

or pharmaceutically acceptable salt thereof, wherein each of q, X, R$^1$, R$^2$, R$^4$, and R$^6$ is independently as defined in any embodiment described herein.

In certain embodiments, the compound is:

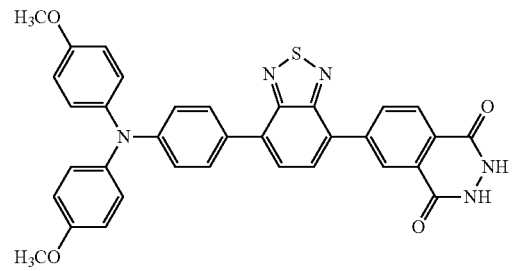 [SMILES: COc1ccc(N(c2ccc(OC)cc2)c2ccc(-c3ccc(-c4ccc5c(=O)[nH][nH]c(=O)c5c4)c4nsnc34)cc2)cc1]

or a pharmaceutically acceptable salt thereof.

The compounds described herein can be optionally conjugated to a targeting agent that is capable of selectively binding to a target of interest. The targeting agent can be an antibody, an antibody fragment (such as Fab, Fab', F(ab')$_2$, Fv), single chain (ScFv)) a peptide, an aptamer, or a small molecule, such as a carbohydrate, polynucleotide, lipid, polypeptide, etc.

The targeting agent can be covalently bonded directly to the compound described herein are via an optional linker. In certain embodiments, the targeting agent is covalently bonded to the compound a linker having the formula —(CH$_2$)$_t$R$^8$, wherein "-" represents the site of attachment of the linker to the compound described herein; t is a whole number selected from 0-6; and R$^8$ is —N$_3$, —OH, —CO$_2$H, —NH$_2$, —C≡CH, —Br, —I, or N-maleimide. In such instances, the targeting agent may be covalently attached by reaction with the functional group present at R$^8$. The covalent attachment of the targeting agent and the selection of the functional group present at R$^8$ are within the skill of a person of ordinary skill in the art.

Also provided herein is a compound of Formula 1A:

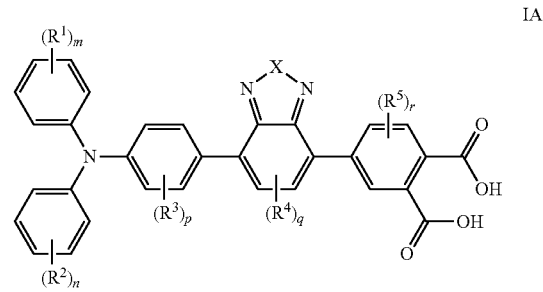

or a pharmaceutically acceptable salt or zwitterion thereof, wherein each of m, n, p, q, X, R$^1$, R$^2$, R$^3$, R$^4$, and R$^5$ is independently as described herein.

In certain embodiments, the compound of Formula 1A is:

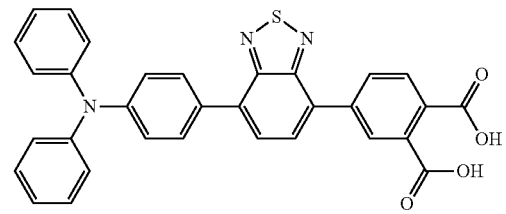 [SMILES: O=C(O)c1ccc(-c2ccc(-c3ccc(N(c4ccccc4)c4ccccc4)cc3)c3nsnc23)cc1C(=O)O]

or a pharmaceutically acceptable salt or zwitterion thereof.

The present disclosure also provides a pharmaceutical composition comprising a compound or nanoparticle described herein and at least one pharmaceutically acceptable excipient and/or pharmaceutically acceptable carrier.

The compound or nanoparticle described herein and their pharmaceutically acceptable salts can be administered to a subject either alone or in combination with pharmaceutically acceptable carriers or diluents in a pharmaceutical composition according to standard pharmaceutical practice. The compound or nanoparticle can be administered parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise an amount of the compound or nanoparticle described herein, formulated together with one or more pharmaceutically acceptable carriers (additives) and/or diluents. The pharmaceutical compositions of the present disclosure may be specially formulated for administration in liquid form, including those adapted for the following: (1) parenteral administration, for example, by intravenous as, for example, a sterile solution or suspension.

As set out herein, certain embodiments of the compound or nanoparticle described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of a compound of the present disclosure. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of the compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the compound include the step of bringing into association a compound described herein with the carrier and, optionally, one or more accessory ingredients. In general, the formulations are prepared by uniformly and intimately bringing into association a compounds described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more compounds described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars (such as sucrose), alcohols, non-ionic surfactants (such as Tween 20) antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The present disclosure also provides a nanoparticle comprising a compound as described herein. In certain embodiments, the nanoparticle further comprises a non-ionic surfactant. The non-ionic surfactant can be a polyalkylene glycol. Exemplary polyalkylene glycols polyethylene glycol, polypropylene glycol, and mixtures and copolymers thereof. In certain embodiments, the non-ionic surfactant is poly(ethylene glycol)-block-poly(propylene glycol).

The average hydrodynamic size of the nanoparticle in phosphate buffered saline solution at pH 7.4 can be between 10-2,500 nm, 10-2,000 nm, 10-1,500 nm, 10-1,000 nm, 10-500 nm, 10-100 nm, 10-50 nm, 10-40 nm, 10-30 nm, 20-30 nm, 20-50 nm, 30-50 nm, or 40-50 nm.

The compounds described herein can be prepared using well known conventional synthetic methodologies. A person of ordinary skill in the art can readily prepare the compounds described herein based on common general knowledge and methods disclosed herein.

In examples below, TBL is prepared by Suzuki C—C coupling reaction. Other metal mediated C—C coupling reactions can be used to prepare the compounds described herein. The selection of the C—C coupling reaction will be determine, based in part, on functional group compatibility of the starting materials.

In certain embodiments, the compounds described herein are prepared by contacting a compound of Formula 4:

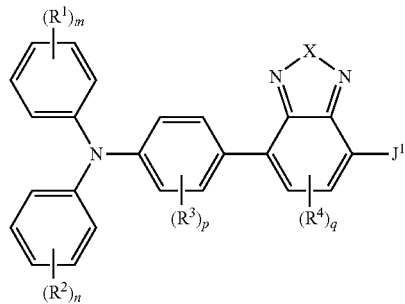

4 or a pharmaceutically acceptable salt thereof, wherein each of m and n are independently a whole number selected from 0-5;

p if a whole number selected from 1-4;

q is a whole number selected from 1-2;

t is a whole number selected from 0-6;

$J^1$ is halide, mesylate, tosylate, triflate, —B(OR$^9$)$_2$ or —Sn(R$^{10}$)$_3$;

X is O, S, or NR$^7$;

each of R$^1$, R$^2$, R$^3$, and R$^4$ is independently for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, (CH$_2$)$_t$R$^8$;

R$^7$ for each occurrence is independently hydrogen, alkyl, cycloalkyl, alkenyl, alkynyl, aryl, heterocycloalkyl, and heteroaryl;

R$^8$ for each occurrence is independently —N$_3$, —OH, —CO$_2$H, —NH$_2$, —C≡CH, —Br, —I, or N-maleimide; and R for each occurrence is independently hydrogen, alkyl, cycloalkyl, alkenyl, alkynyl, aryl, heterocycloalkyl, and heteroaryl;

a compound of Formula 5:

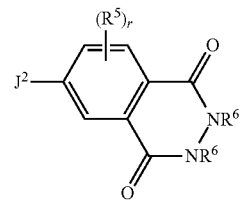

5 r is a whole number selected from 1-3;

$J^2$ is halide, mesylate, tosylate, triflate, —B(OR$^9$)$_2$, or —Sn(R$^{10}$)$_3$;

R$^5$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O) NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, (CH$_2$)$_t$R$^8$;

R$^6$ for each occurrence is independently hydrogen, alkyl, cycloalkyl, alkenyl, alkynyl, aryl, heterocycloalkyl, or heteroaryl;

R$^9$ is hydrogen, alkyl, cycloalkyl, or aryl; or two instances of R$^9$ together with the oxygen to which they are attached form a 5-6 membered optionally heterocylic ring; and each R$^{10}$ is independently for each occurrence alkyl; and a catalyst thereby forming the compound, wherein if $J^1$ is halide, mesylate, tosylate, or triflate, then $J^2$ is —B(OR$^9$)$_2$ or —Sn(R$^{10}$)$_3$; and if $J^1$ is —B(OR$^9$)$_2$ or —Sn(R$^{10}$)$_3$, then $J^2$ is halide, mesylate, tosylate, or triflate.

The catalyst may be a palladium catalyst. Palladium catalysts can be added directly to the reaction mixture or added as a pre-catalyst, which is converted to the catalyst in situ. In certain embodiments, the palladium catalyst or pre-catalyst is selected from the group consisting of Pd/C, bis(dibenzylideneacetone)palladium(0), [1,1'-bis(diphenylphosphino)ferrocene]dichloropalladium(II), bis(triphenylphosphine) palladium(II) diacetate, bis(triphenylphosphine)palladium(II) dichloride, dichloro(1,5-cyclooctadiene)palladium(II), palladium(II) acetate, palladium(II) acetylacetonate, palladium (II) chloride, tetrakis(triphenylphosphine)palladium(0), tris(dibenzylideneacetone)dipalladium(0), and the like. In certain embodiments, the reaction further comprises a ligand, such PR'$_3$, wherein each R' is independently selected from optionally substituted alkyl, optionally substituted cycloalkyl, optionally substituted aryl, or optionally substituted heteroaryl. In certain embodiments the palladium catalyst or pre-catalyst is tetrakis(triphenylphosphine)palladium(0).

In instances in which $J^1$ or $J^2$ is —B(OR$^9$)$_2$, the reaction may further comprise a base, such as organic or inorganic base. Exemplary bases include, but are not limited to, K$_2$CO$_3$, Na$_2$CO$_3$, Cs$_2$CO$_3$, NaOH, KOH, NaHCO$_3$, Na$_3$PO$_4$, and KF. In certain embodiments the base is K$_2$CO$_3$.

In instances in which $J^1$ or $J^2$ is —Sn(R$^{10}$)$_3$, the reaction may further comprise a fluoride salt and optionally a copper salt. Exemplary fluoride salts include, but are not limited to, KF and CsF. Exemplary copper salts include, but are not limited to, CuBr or CuI.

The coupling reaction can be conducted a wide range of solvents, such as DMF (dimethylformamide), DME (dimethoxyethane), DMA (dimethylacetamide), NMP (N-methylpyrrolidone), THF (tetrahydrofuran), toluene, methanol, ethanol, iso-propanol, n-butanol, water, and mixtures thereof. In certain embodiments, the reaction is conducted in THF/water.

The compounds and nanoparticles described herein can be used to detect reactive oxygen species in a sample. Accordingly, the present disclosure also provides a method of detecting a reactive oxygen species in a sample suspected of containing the reactive oxygen species, the method comprising: contacting the sample with a compound or nanoparticle described herein and detecting the chemiluminescence of the compound or nanoparticle.

The reactive oxygen can be peroxide, superoxide, hydroxyl radical, singlet oxygen, or combinations thereof. In certain embodiments, the reactive oxygen species is an organic peroxide, an organic hydroperoxide, and combinations thereof.

The sample may be comprise a food stuff, an environmental material (e.g., soil, air, water, and the like), or a biological material, such as a sample obtained from a mammal, fungus, plant, bacteria, or virus. In certain embodiments, the sample comprises tissue or body fluid obtained from a subject. In certain embodiments, the sample comprises a cancer.

In instances in which the sample comprises a cancer, the cancer can be a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

The step of detecting the chemiluminescence of the compound or nanoparticle can comprise using a spectrometer to detect chemiluminescence of the compound of nanoparticle in the near infrared region. In certain embodiments, the chemiluminescence of the compound of nanoparticle is detected between 750 to 1,400 nm or 550 to 800 nm.

The compounds and nanoparticles described herein can be used in a wound as a reactive oxygen species sensor for wound-healing monitoring. The compounds and nanoparticles described herein can also be used in the form of an injectable, implant, bandage, suture, or the like in applications in which monitoring reactive oxygen species of the skin or underlying tissue would be beneficial, such as in wound healing monitoring and surgeries. The compounds and nanoparticles described herein can also be used to measure reactive oxygen species present in the circulatory system or for monitoring pulmonary function. The compounds and nanoparticles described herein can also be used in oncology applications to determine the degree of hypoxia in a tissue or an organ. In certain embodiments, the compounds and nanoparticles described herein are used to monitor tumor growth in an animal, including but not limited to, mouse or rat models used in oncology pharmaceutical and diagnostic research and discovery, e.g., cancer therapy dosing or monitoring of tumor metabolism.

The method of detecting a reactive oxygen species in the sample can further comprise determining the concentration of the reactive oxygen species in the sample. In such instances, the method can further comprise comparing the chemiluminescence of the compound or nanoparticle using a spectrometer with one or more calibration curves prepared using the interrelation between the chemiluminescence of known concentrations of reactive oxygen species in standard samples comprising the compound or nanoparticle; and determining the concentration of reactive oxygen in the sample.

The interrelation between the chemiluminescence of the sample and the compound or nanoparticle in standard samples having known concentrations of reactive oxygen species can be determined by preparing a series of standard samples, preferably comprising a similar analyte matrix, containing the compound or nanoparticle and known concentrations of reactive oxygen species and determining the absorbance of each standard sample having a different reactive oxygen species concentration using a spectrometer. One or more calibration curves can be prepared using the interrelation between absorbance of known concentrations of reactive oxygen species in standard samples comprising the compound or nanoparticle. The concentration of reactive oxygen species in the sample can then be determined by comparing the chemiluminescence of the test sample with the calibration curve.

EXAMPLES

All chemicals for the synthesis were purchased from Sigma-Aldrich, J&K chemistry and Energy Chemical (China) as received without further purification. A non-ionic surfactant, poly(ethylene glycol)-block-poly(propylene glycol) (average molecular weight ~12,600 g/mol), sold under the trademark Pluronic® F127 (99%) by Aldrich Co., Ltd. Sodium hypochlorite (NaClO, active chlorine ≥5.2%) and hydrogen peroxide (30%) were provided by Sinopharm Chemical Reagent Co., Ltd. Dulbecco's modified eagle medium (DMEM), Fetal bovine serum (FBS), and penicillin-streptomycin were purchased from M&C gene technology (Beijing) Ltd. 3-(4,5-Dimethyl-2-Thiazolyl)-2,5-Diphenyl Tetrazolium Bromide (MTT) was obtained from Energy chemical Co., Ltd.

$^1$H NMR and $^{13}$C NMR spectra were measured by the Bruker ARX 400 NMR spectrometer. High resolution mass spectra (HRMS) were measured by GCT premier CAB048 mass spectrometer operating in a MALDI-TOF mode. UV-Vis absorption spectra were measured on PerkinElmer Lambda 365 Spectrophotometer. Photoluminescence (PL) spectra were measured by Fluorolog®$^3$ Spectrofluoromete. Absolute fluorescence quantum yield was measured by Hamamatsu quantum yield spectrometer C11347 Quantaurus QY. The size (diameter, nm) of TBL dots were measured by the dynamic light scattering (DLS, Malvern Zetasizer Nano ZS90, USA). The morphology of TBL dots were observed by transmission electron microscope (TEM, Hitachi HT7700, Japan).

Example 1—Synthesis of TBL

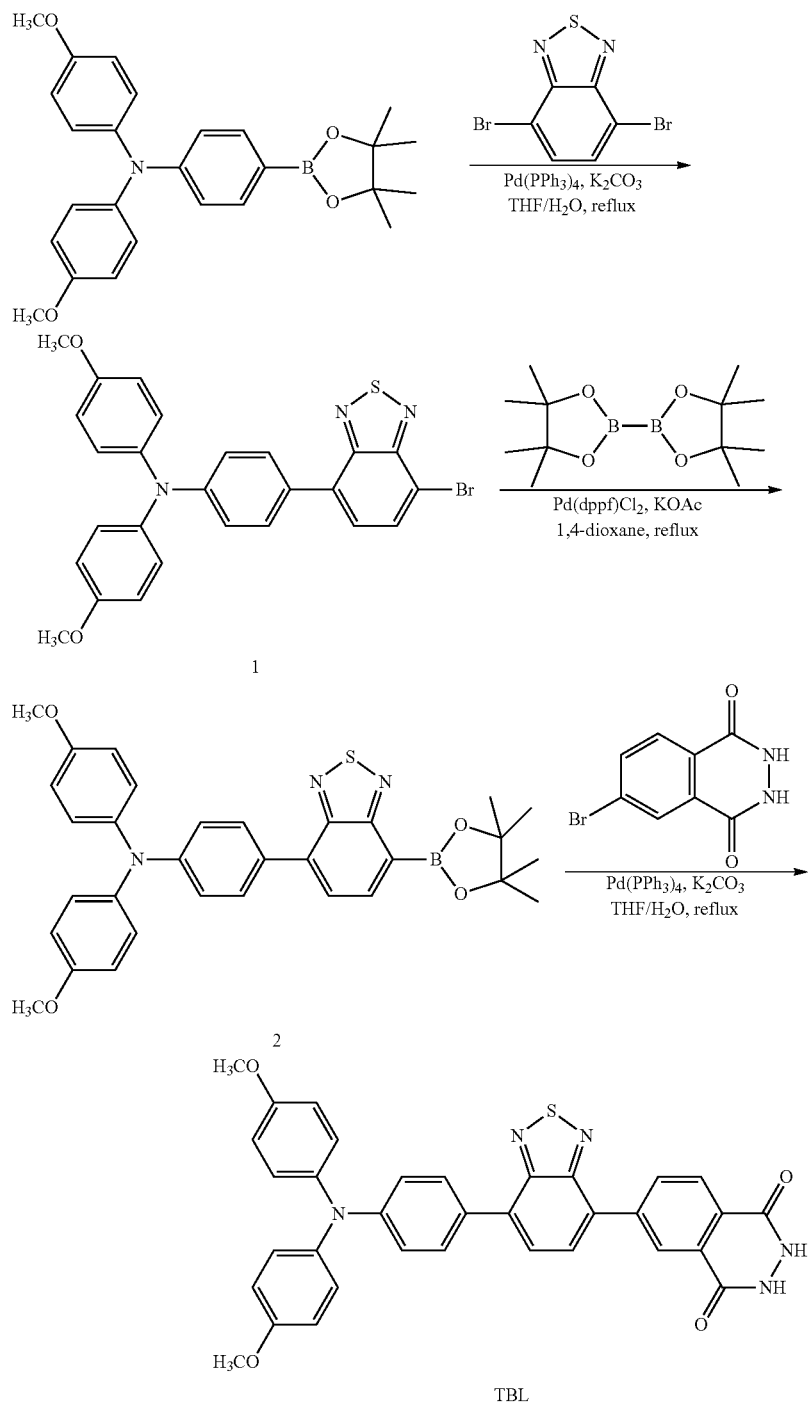

Scheme 1. Synthetic Route to TBL

Synthesis of 4-(7-bromobenzo[c][1,2,5]thiadiazol-4-yl)-N,N-bis(4-methoxyphenyl) aniline (Compound 1). In a 100 mL two-neck round-bottom flask, 4-methoxy-N-(4-methoxyphenyl)-N-(4-(4,4,5,5-tetramethyl-1,3,2-dioxaborolan-2-yl)phenyl)aniline (2.16 g, 5 mmol), 4,7-dibromobenzo[c][1,2,5]thiadiazole (1.75 g, 6 mmol) and Pb(PPh3)4 (30 mg, 0.026 mmol) were dissolved in THF (40 mL) and K2CO3 solution (2 M, 5 mL) under the protection of N2, then the mixture was heated to 80° C. and stirred for 12 h. After that, the reaction mixture was cooled to room temperature and exacted with DCM (40 mL×3), then the organic layer was dried over MgSO4 and concentrated. The crude product was purified by silica gel chromatography with hexane/ethyl acetate (3:1, v/v) to obtain compound 1 as orange power (1.96 g, 76%). $^1$H NMR (400 MHz, Chloroform-d) δ 7.88 (d, J=7.7 Hz, 1H), 7.77-7.72 (m, 2H), 7.51 (d, J=7.6 Hz, 1H), 7.17-7.11 (m, 4H), 7.06-7.00 (m, 2H), 6.89-6.84 (m, 4H), 3.81 (s, 6H). $^{13}$C NMR (101 MHz, Chloroform-d) δ 156.33, 153.99, 153.26, 149.34, 140.37, 133.83, 132.43, 129.77, 127.85, 127.19, 126.93, 119.49, 114.83, 111.68, 55.52. HRMS (MALDI-TOF, m/z): [M] calcd for $C_{26}H_{20}BrN_3O_2S$ 517.0460, found 517.0488.

Synthesis of 4-methoxy-N-(4-methoxyphenyl)-N-(4-(7-(4,4,5,5-tetramethyl-1,3,2-dioxaborolan-2-yl)benzo[c][1,2,5]thiadiazol-4-yl)phenyl)aniline (Compound 2). In a 50 mL two neck round-bottom flask, compound 1 (517.04 mg, 1 mmol), bis(pinacolato)diboron (380.91 mg, 1.5 mmol), KOAc (294.45 mg, 3 mmol) and Pd(dppf)Cl$_2$ (35 mg, 0.05 mmol) were dissolved in anhydrous dioxane (20 mL) under N$_2$ atmosphere, then the reaction mixture was stirred at 110° C. for 24 h. After cooling to room temperature, the crude product was extracted with DCM (30 mL×3) and dried over MgSO$_4$, then the organic layer was concentrated and purified by silica gel chromatography with hexane/ethyl acetate (3:1, v/v) to obtain compound 2 as red power (407 mg, 72%). $^1$H NMR (400 MHz, Chloroform-d) δ 8.22 (d, J=7.0 Hz, 1H), 7.84-7.81 (m, 2H), 7.64 (d, J=7.1 Hz, 1H), 7.15-7.12 (m, 4H), 7.06-7.02 (m, 2H), 6.88-6.84 (m, 4H), 3.81 (s, 6H), 1.45 (s, 12H). $^{13}$C NMR (101 MHz, Chloroform-d) δ 158.36, 156.26, 153.36, 149.30, 140.46, 139.37, 137.02, 130.05, 128.71, 127.21, 127.12, 125.84, 119.56, 114.80, 84.25, 55.52, 24.93. HRMS (MALDI-TOF, m/z): [M+H$^+$] calcd for, $C_{32}H_{33}BN_3O_4S$ 566.2285, found 566.2254.

Synthesis of 6-bromo-2,3-dihydrophthalazine-1,4-dione (compound 3). In a 250 mL two-neck round-bottom flask, 5-bromophthalic anhydride (5.9 g, 26 mmol) was added into acetic acid (60 mL) under N$_2$ atmosphere, then the mixture was stirred at 125° C. for 1 h. After cooling to room temperature, hydrazine monohydrate (1.325 mL, 27.3 mmol) was injected dropwise into the mixture, then the reaction mixture was refluxed at 125° C. for 30 min. After cooling to room temperature, white solid precipitated from the solvent and was separated by filtration. The product was dissolved in 5% NaOH (15 mL) and acidified by AcOH (1.5 mL), then the white solid precipitated again. The solid was washed water (100 mL) and MeOH (100 mL) to obtained compound 3 as white solid (5.22 g, 84%). 1H NMR (400 MHz, DMSO-d6) δ 11.74 (s, 2H), 8.15 (s, 1H), 8.04 (dd, J=8.5, 1.9 Hz, 1H), 7.98 (d, J=8.5 Hz, 1H).

Synthesis of 6-(7-(4-(bis(4-methoxyphenyl)amino)phenyl)benzo[c][1,2,5] thiadiazol-4-yl)-2,3-dihydrophthalazine-1,4-dione (TBL). In a 100 mL two-neck round-bottom flask, compound 2 (56.2 mg, 0.1 mmol), compound 3 (24.0 mg, 0.1 mmol) and Pb(PPh$_3$)$_4$ (15 mg, 0.013 mmol) were dissolved in THF (20 mL) and K$_2$CO$_3$ solution (2 M, 1 mL) under N$_2$ atmosphere, then the solution was refluxed at 80° C. for 12 h. After cooling to room temperature, the pH of the solution was adjust to 7.0 with HCl (0.1 M) solution, then the crude product was extracted with DCM (30 mL×3) and dried over MgSO$_4$, the organic layer was concentrated and purified by silica gel chromatography with DCM/MeOH (5:1, v/v) to obtain compound TBL as red power (27.5 mg, 46%). 1H NMR (400 MHz, DMSO-d6) δ 8.76 (s, 1H), 8.46 (d, J=7.6 Hz, 1H), 8.22 (d, J=8.0 Hz, 1H), 8.10 (d, J=7.4 Hz, 1H), 7.92 (d, J=8.9 Hz, 3H), 7.16-7.11 (m, 4H), 7.00-6.95 (m, 4H), 6.90 (d, J=8.8 Hz, 2H), 3.77 (s, 6H). 13C NMR (101 MHz, DMSO-d6) δ 156.63, 153.84, 152.15, 147.92, 140.10, 139.35, 133.05, 130.53, 130.22, 130.13, 128.09, 127.69, 127.20, 124.83, 118.80, 115.57, 115.15, 114.19, 55.75, 37.74, 29.65, 22.56, 14.42. HRMS (MALDI-TOF, m/z): [M+H$^+$] calcd for $C_{34}H_{26}N_5O_4S$ 600.1707, found 600.1691.

Example 2—Synthesis of TBLCOOH

Synthesis of 4-(7-(4-(bis(4-methoxyphenyl)amino)phenyl)benzo[c][1,2,5] thiadiazol-4-yl)phthalic acid (TBLCOOH). In a 20 mL beaker, TBL (12 mg, 0.02 mmol) was dissolved in THF (5 mL), then NaClO solution (5%, 72 μL, 0.1 mM) and H$_2$O$_2$ solution (30%, 10 μL, 0.1 mM) in H$_2$O (5 mL) were added and stirred for 1 h. The solvent was then concentrated and the crude product was washed with diethyl ether (10 mL×3) to obtain TBLCOOH as the red powder (9 mg, 74%). 1H NMR (400 MHz, DMSO-d6) δ 8.83 (s, 1H), 8.33 (d, J=8.2 Hz, 1H), 8.14 (dd, J=8.2, 2.1 Hz, 1H), 7.99 (d, J=7.4 Hz, 1H), 7.91 (dd, J=8.2, 3.3 Hz, 3H), 7.18-7.10 (m, 4H), 7.02-6.94 (m, 4H), 6.90 (dt, J=9.0, 2.2 Hz, 2H), 3.76 (s, 6H). HRMS (MALDITOF, m/z): [M] calcd for $C_{34}H_{25}N_3O_6S$ 603.1464, found 603.1448.

Example 3—Preparation of TBL Dots

TBL (5 mg) and Pluronic® F127 (0.25 g) were dissolved in 2 mL of THF to get a homogeneous mixture. The mixture was then dropped into 6 mL of 0.1 M pH 7.4 PBS buffer and sonicated for 10 min. After rotary evaporation to remove all THF, the TBL dots solution was filtrated with 0.2 μm filter, the obtained solutions were then air-tight stored in 4° C. for followed experiments.

Example 4—Stability of TBL Dots

The TBL dots of different concentrations in PBS solution (0.1 M, pH=7.4) were stored in dark at 4° C., and the average diameter, PDI, aggregation of which were monitored in four weeks. Moreover, we also detected the average diameter, and PDI of the TBL dots in DMEM containing 10% FBS.

Example 5—Evaluation of the CL Response of TBL Dots Against Common ROS

We evaluated the CL response of TBL dots against common ROS, such as H$_2$O$_2$, hypochlorite anion (ClO$^-$), hydroxyl radical (OH$^-$), superoxide anion radical (O$_2$.$^-$) and $^1$O$_2$. The ROS were generated according to the reported methods. OH. was produced by Fenton reaction using H$_2$O$_2$ and FeSO$_4$, O2.$^-$ was generated during the oxidation of xanthine by xanthine oxidase. The experiments were tested in PBS buffer solution (0.1 M, pH=7.4).

Example 6—the CL Response of TBL Dots in Various Conditions

We evaluated the CL response of TBL dots in different pH, plasma solutions, and the kinetic of CL emission of TBL dots oxidized by $^1$O$_2$. To detect the effect of pH in the CL response of TBL dots, TBL dots (1.5 mM) in PBS (0.1 M, pH=7.4) or in PBS (0.1 M, pH=6.5) were applied to react with $^1$O$_2$ (2 mM). To detect the effect of biological potential interferents in the CL response of TBL dots, TBL dots (0.5 mM) in PBS (0.1 M, pH=7.4) or in PBS (0.1 M, pH=7.4) containing 2% mouse plasma were applied to react with $^1$O$_2$ (2 mM). We also monitored the change of CL intensity of TBL dots (2 mM) post the addition of H$_2$O$_2$ (10 mM) and NaClO (10 mM).

Example 7—Determination of the Detection Limit

The detection limit=3 S.D./k, where k is the slope of the curve and S.D. represents the standard deviation for the CL intensity of TBL dots in the absence of $^1O_2$.

Example 8—Cytotoxicity Studies

To evaluate the biocompatibility and security of TBL dots, the cytotoxicity of TBL dots was assessed through cell viability by using NIH 3T3 cells (mouse embryonic fibroblasts, normal cell line) and 4T1 cells (mouse breast cancer cell, cancer cell line) with an MTT assay. Cells were seeded in 96-well plates at a density of $5 \times 10^4$ cells mL-1 and cultured in standard medium for 24 h. The cells were then incubated with various concentrations of TBL dots (0.5, 1.25, 2.5, 5, 10, 20, 50, 100, $200 \times 10^{-6}$ M) in the dark for 24 h. After cells were washed by PBS twice, 100 μL of freshly prepared MTT solution (0.5 mg/mL) was added into each well. The MTT solution was carefully removed after 3 h of incubation, and 150 μL of DMSO was added into each well to dissolve all the purple crystals formed. The absorbance of MTT at 570 nm was measured by the microplate reader (Varioskan LUX, Thermo Scientific, USA). Cell viability was calculated using the ratio of the absorbance of the cells treated with TBL dots to that of the cells incubated with the culture medium. Each of above experiment was repeated three times. The cytotoxicity of $H_2O_2$ was assessed through cell viability by using 4T1 cells with an MTT assay. Cells were seeded in 96-well plates at a density of $5 \times 10^4$ cells mL-1 and cultured in standard medium for 24 h. The cells were then incubated with various concentrations of $H_2O_2$ for 6 h, 12 h, and 24 h. After cells were washed by PBS twice, 100 μL of freshly prepared MTT solution (0.5 mg/mL) was added into each well. The MTT solution was carefully removed after 3 h of incubation, and 150 μL of DMSO was added into each well to dissolve all the purple crystals formed. The absorbance of MTT at 570 nm was measured by the microplate reader. We also evaluated the cytotoxicity of $H_2O_2$ to 4T1 cells by FDA/propidium iodide (PI) staining. Cells were seeded in 6-well plates and cultured in standard medium for 24 h. The cells were then incubated with $H_2O_2$ (1 mM) for 24 h. After cells were washed by PBS twice, 1 mL of freshly prepared FDA (5 μg/mL) and PI solution (20 μg/mL) was added into each well. The dyes solution was carefully removed after 10 min of incubation. The images of cells were captured by luminescence microscope post cells washed by PBS for 3 times. The green signal represents living cells, whereas the red signal represents dead cells. To evaluate the biocompatibility of TBL dots, we performed hemolytic assay using mouse erythrocytes. The hemoglobin release in the plasma was as an indicator of red blood lysis in the in vitro hemolysis assay. The isolated mouse erythrocytes were incubated with TBL dots solutions at 37° C., 100 rpm for 2 h. Phosphate-buffered saline (PBS) was used as negative control, and 0.2% of Triton-X100 was acted as positive control. After 2 h of incubation, intact erythrocytes were pelleted and the supernatants containing hemoglobin released from lysed erythrocytes were estimated photometrically by a microplate reader at 570 nm.

Example 9—Tissue Penetration Depth Evaluation

In vitro chemiluminescence (CL) imaging and fluorescence imaging were performed using the Maestro EX in vivo imaging system (Caliper IVIS® Lumina II) under bioluminescence and fluorescence modes, respectively. For in vitro fluorescence imaging of the samples, the fluorescence images were acquired with the filter of Cy 5.5 upon excitation at 465 nm. For in vitro CL imaging of the TBL dots solutions, the CL images were acquired with an open filter. CL images of nanoparticles in 96-well plate were taken through biological tissue specimen of varying thickness. In vitro CL imaging was performed after addition of $H_2O_2$ and NaClO to each well, immediately. The FL images were captured post-CL imaging.

Example 10—4T1 Breast-Tumor-Bearing Mouse Model

Six-week-old female BALB/c mice were used to establish the breast cancer mouse model. 100 μL of 4T1 breast cancer cells ($2 \times 10^7$) in DMEM free of fetal bovine serum was injected subcutaneously into the right rear flank of each mice. When the volume of tumor reached approximately 500 $mm^3$, the mice were submitted to tumor imaging. Healthy BALB/c mice without tumor was used as control group.

Example 11—In Vivo CL Imaging

To study the change of CL of TBL dots in vivo, C57/J mice anesthetized were subcutaneously injected with 50 μL of TBL dots solution ($2 \times 10^{-3}$ M), 50 μL of $H_2O_2$ (1 mM), and 50 μL of NaClO (1 mM) into the same field of back. The CL images were captured post-injection for different time.

To validate whether TBL NPs can distinguish tumor tissue from normal tissue, 4T1 breast tumor-bearing mice anesthetized were intratumorally injected with 200 μL of TBL dots solution ($2 \times 10^{-3}$ M) each mouse. For the comparison, equivalent dose of TBL dots solution was subcutaneously injected into back. The CL images were taken immediately as mentioned above. And then 50 μL of $H_2O_2$ (400 mM) was injected into tumor or back near the site of TBL dots solution injection before CL images caption. The mice were anesthetized before tumor bearing mice was imaged by the Caliper IVIS Lumina II system. The IVIS Lumina Living Image software was employed to quantify the imaging results.

What is claimed is:
1. A compound having Formula 1:

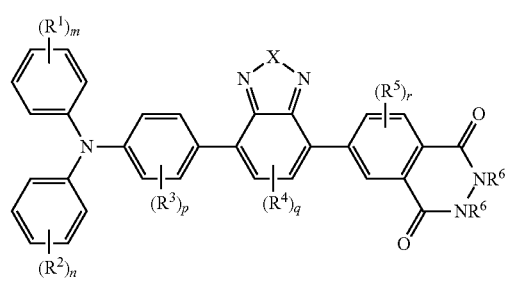

or a pharmaceutically acceptable salt thereof, wherein
each of m and n are independently a whole number selected from 1-5;
p if a whole number selected from 1-4;
q is a whole number selected from 1-2;
r is a whole number selected from 1-3;
t is a whole number selected from 0-6;
X is O, S, or $NR^7$;

each of $R^1$, $R^2$, $R^3$, $R^4$, and $R^5$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, and —(CH$_2$)$_r$R$^8$;

$R^6$ for each occurrence is independently hydrogen, alkyl, cycloalkyl, alkenyl, alkynyl, aryl, heterocycloalkyl, or heteroaryl;

$R^7$ for each occurrence is independently hydrogen, alkyl, cycloalkyl, alkenyl, alkynyl, aryl, heterocycloalkyl, or heteroaryl;

$R^8$ for each occurrence is independently —N$_3$, —OH, —CO$_2$H, —NH$_2$, —C≡CH, —Br, —I, or N-maleimide; and R for each occurrence is independently hydrogen, alkyl, cycloalkyl, alkenyl, alkynyl, aryl, heterocycloalkyl, or heteroaryl.

2. The compound of claim 1, wherein each of m, n, p, and r is 1.

3. The compound of claim 1, wherein each of $R^1$, $R^2$, $R^3$, $R^4$, and $R^5$ is independently for each occurrence is independently selected from the group consisting of hydrogen, halide, —OR, —NR$_2$, —N(R)(C=O)R, —O(C=O)R, —N(R)(C=O)OR, —N(R)(C=O)NR$_2$, alkyl, cycloalkyl, aryl, heterocycloalkyl, and heteroaryl.

4. The compound of claim 2, wherein each of $R^1$ and $R^2$ is independently for each occurrence is independently selected from the group consisting of hydrogen, —OR, —NR$_2$, —N(R)(C=O)R, —O(C=O)R, —N(R)(C=O)OR, —N(R)(C=O)NR$_2$, alkyl, aryl, heterocycloalkyl, and heteroaryl; and $R^4$ is halide.

5. The compound of claim 1, wherein X is O, S, or NR$^7$, wherein $R^7$ is hydrogen or alkyl.

6. The compound of claim 1, wherein the compound has Formula 2:

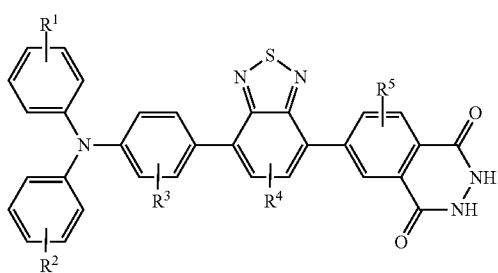

wherein each of $R^1$, $R^2$, $R^3$, $R^4$, and $R^5$ is independently hydrogen, F, alkyl, unsaturated alkyl, heteroalkyl, cycloalkyl, heterocycloalkyl, aryl, heteroaryl, carboxyl group, amino group, sulfonic group, alkylthio, or alkoxy group.

7. The compound of claim 1, wherein the compound has Formula 3:

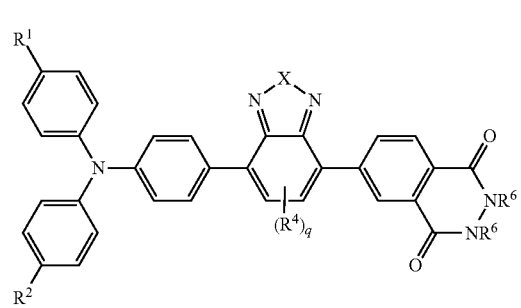

or a pharmaceutically acceptable salt thereof, wherein q is a whole number selected from 1-2;

t is a whole number selected from 0-6;

X is O, S, or NR$^7$;

each of $R^1$ and $R^2$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, and —(CH$_2$)$_t$R$^8$;

$R^4$ is hydrogen, alkyl, or halide;

$R^6$ for each occurrence is independently hydrogen or alkyl;

$R^7$ for each occurrence is independently hydrogen or alkyl;

$R^8$ for each occurrence is independently —N$_3$, —OH, —CO$_2$H, —NH$_2$, —C≡CH, —Br, —I, or N-maleimide; and R for each occurrence is independently hydrogen, alkyl, cycloalkyl, alkenyl, alkynyl, aryl, heterocycloalkyl, or heteroaryl.

8. The compound of claim 7, wherein X is S; each of $R^1$ and $R^2$ is —OR; and $R^4$ and $R^6$ is hydrogen.

9. The compound of claim 1, wherein the compound is:

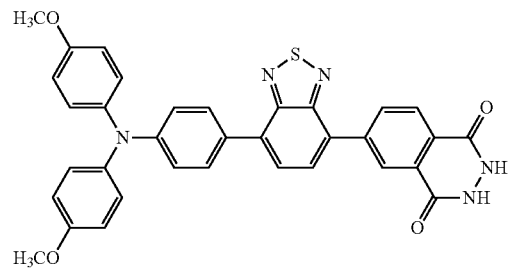 [SMILES: COc1ccc(N(c2ccc(OC)cc2)c2ccc(-c3ccc(-c4ccc5c(=O)[nH][nH]c(=O)c5c4)c4nsnc34)cc2)cc1]

or a pharmaceutically acceptable salt thereof.

10. A method of preparing the compound of claim 1, the method comprising:

contacting a compound of Formula 4:

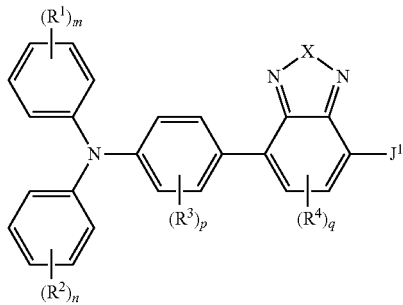

or a pharmaceutically acceptable salt thereof, wherein
each of m and n are independently a whole number selected from 0-5;
p if a whole number selected from 1-4;
q is a whole number selected from 1-2;
t is a whole number selected from 0-6;
$J^1$ is halide, mesylate, tosylate, triflate, —B(OR$^9$)$_2$ or —Sn(R$^{10}$)$_3$;
X is O, S, or NR$^7$;
each of R$^1$, R$^2$, R$^3$, and R$^4$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, and —(CH$_2$)$_t$R$^8$;
R$^7$ for each occurrence is independently hydrogen, alkyl, cycloalkyl, alkenyl, alkynyl, aryl, heterocycloalkyl, or heteroaryl;
R$^8$ for each occurrence is independently —N$_3$, —OH, —CO$_2$H, —NH$_2$, —C≡CH, —Br, —I, or N-maleimide; and
R for each occurrence is independently hydrogen, alkyl, cycloalkyl, alkenyl, alkynyl, aryl, heterocycloalkyl, or heteroaryl;
a compound of Formula 5:

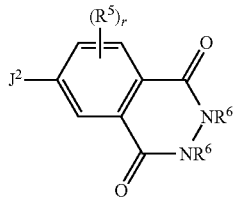

r is a whole number selected from 1-3;
$J^2$ is halide, mesylate, tosylate, triflate, —B(OR$^9$)$_2$, or —Sn(R$^{10}$)$_3$;
R$^5$ for each occurrence is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —N(R)(C=O)NR$_2$, —O(C=O)NR$_2$, —(S=O)R, —SO$_2$R, —SO$_2$OR, —SO$_2$NR$_2$, —N(R)SO$_2$R, alkyl, cycloalkyl, alkenyl, alkynyl, aryl, heterocycloalkyl, heteroaryl, and —(CH$_2$)$_t$R$^8$;
R$^6$ for each occurrence is independently hydrogen, alkyl, cycloalkyl, alkenyl, alkynyl, aryl, heterocycloalkyl, or heteroaryl;
R$^9$ is hydrogen, alkyl, cycloalkyl, or aryl; or two instances of R$^9$ together with the oxygen to which they are attached form a 5-6 membered optionally heterocylic ring; and
R$^{10}$ for each occurrence is independently alkyl; and
a catalyst thereby forming the compound of claim 1, wherein if $J^1$ is halide, mesylate, tosylate, or triflate, then $J^2$ is —B(OR$^9$)$_2$ or —Sn(R$^{10}$)$_3$; and if $J^1$ is —B(OR$^9$)$_2$ or —Sn(R$^{10}$)$_3$, then $J^2$ is halide, mesylate, tosylate, or triflate.

11. A nanoparticle comprising the compound of claim 1.

12. The nanoparticle of claim 11 further comprising a non-ionic surfactant.

13. The nanoparticle of claim 12, wherein the non-ionic surfactant is a polyalkylene glycol.

14. The nanoparticle of claim 12, wherein the average hydrodynamic size of the nanoparticle in phosphate buffered saline solution at pH 7.4 is between 10-100 nm.

15. A pharmaceutical composition comprising the compound of claim 1 and at least one pharmaceutically acceptable excipient.

16. A method of detecting a reactive oxygen species in a sample suspected of containing the reactive oxygen species, the method comprising: contacting the sample with a compound of claim 1 and detecting the chemiluminescence of the compound.

17. The method of claim 16 further comprising determining the concentration of the reactive oxygen species in the sample based on the detected intensity of chemiluminescence.

18. A method of imaging tissue comprising a reactive oxygen species in a subject, the method comprising: administering a compound of claim 1 to the subject and detecting the chemiluminescence of the compound.

19. The method of claim 18, wherein the compound is administered by injection to the tissue.

20. The method of claim 18, wherein the tissue comprises a cancer cell.

* * * * *